United States Patent [19]

Gruening

[11] Patent Number: 5,554,784

[45] Date of Patent: Sep. 10, 1996

[54] PROCESS FOR PREPARING IODOALKYNYLCARBAMATES HAVING A LOW TENDENCY OF YELLOWING WHEN EXPOSED TO LIGHT

[76] Inventor: Rainer Gruening, 24 Voorhees Dr., Basking Ridge, N.J. 07920

[21] Appl. No.: 271,956

[22] Filed: Jul. 8, 1994

[51] Int. Cl.⁶ ............................................. C07C 261/00
[52] U.S. Cl. ............................... 560/167; 106/18.32
[58] Field of Search ............................................ 560/167

[56] References Cited

U.S. PATENT DOCUMENTS

| | | |
|---|---|---|
| 3,923,870 | 12/1975 | Singer . |
| 4,276,211 | 6/1981 | Singer et al. . |
| 4,297,258 | 10/1981 | Long, Jr. . |
| 4,324,739 | 4/1982 | Zondler ............................ 260/465.4 |
| 4,352,913 | 10/1982 | Zondler ................................ 525/504 |
| 4,366,317 | 12/1982 | Haut ..................................... 544/336 |
| 4,841,088 | 6/1989 | Kusaba et al. . |
| 4,945,109 | 7/1990 | Rayudu . |
| 5,183,927 | 2/1993 | Utsunomiya ........................ 560/167 |
| 5,321,151 | 7/1994 | Lange .................................. 560/167 |
| 5,326,899 | 7/1994 | Lange .................................. 560/164 |

FOREIGN PATENT DOCUMENTS

| | | |
|---|---|---|
| 2056672 | 11/1990 | Canada . |
| 0014032 | 8/1980 | European Pat. Off. . |
| 0513541A2 | 11/1992 | European Pat. Off. . |
| 0539092 | 4/1993 | European Pat. Off. . |

OTHER PUBLICATIONS

Peter D. Gabriele et al., "Protection of Mildewcides and Fungicides from Ultraviolet Light Induced Photo–Oxidation," *J. Coat. Tech.* 56:33–48 (May 1984).

Sigma Chemical Company Catalog, "Biochemicals Organic Compounds For Research And Diagnostic Reagents," p. 196 (1992).

*Primary Examiner*—Michael L. Shippen
*Attorney, Agent, or Firm*—Popham, Haik, Schnobrich & Kaufman, Ltd.

[57] ABSTRACT

A method for preparing iodoalkynylcarbamates exhibiting little or no discoloration or yellowing when incorporated into coating compositions, such as paint compositions, and exposed to sunlight. An alkynol is reacted with freshly distilled isocyanate prepared within 24 to 120 hours prior to reaction with the alkynol, and the resulting product is iodinated to form an iodoalkynylcarbamate that exhibits little or no discoloration or yellowing when incorporated into coating compositions, such as paint compositions, and exposed to ultraviolet light.

3 Claims, No Drawings

PROCESS FOR PREPARING IODOALKYNYLCARBAMATES HAVING A LOW TENDENCY OF YELLOWING WHEN EXPOSED TO LIGHT

BACKGROUND OF THE INVENTION

1. Field of the Invention

The present invention relates to a process for preparing iodoalkynylcarbamates having a low tendency of discoloring or yellowing when exposed to light. More specifically, the invention relates to a process for preparing iodoalkynylcarbamates without employing trialkylamine catalysts.

2. Related Art

Latex paint, in particular white or light colored paint for outdoor application, is subject to discoloration by fungal (mold and mildew) and algae growth. A wide variety of preservatives have been developed to prevent such discoloration. One well-known group of preservatives is derived from iodopropargyl-containing chemical compounds.

Iodopropargyl-containing chemical compounds are known based upon various chemical function groups, such as ethers, esters, etheresters, amides, alcohols, pyrazoles, triazoles, pyridines, aminoacidesters, benzoxazoles, and carbamates. Carbamates have shown good market potential and are commonly used as film fungicides, mold and mildew prohibitors, slime preventing additives, algacides, wood preservatives, cosmetic additives, and disinfectors. Aryl derivatives of carbamates seem to be more suitable for agricultural use than alkyl derivatives. Alkyl derivatives have the general formula:

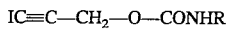

$$IC \equiv C-CH_2-O-CONHR$$

where R is H or a linear or branched alkyl group having 1 to 20 carbon atoms. The two hydrogen atoms at the propargyl group can be substituted by an alkyl group having 1 to 6 carbon atoms.

Alkyl and aryl carbamates are commonly prepared by reacting alcohol with isocyanate to form the carbamate, as described for preparing urethanes in *Organic Synthetic Chemistry*, Vol. 19, No. 11, pp. 775–789 (1961).

Propargylcarbamates are traditionally synthesized according to the following equation:

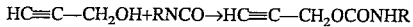

$$HC \equiv C-CH_2OH + RNCO \rightarrow HC \equiv C-CH_2OCONHR$$

where R is an unsubstituted or substituted, saturated or unsaturated, alkyl, cycloalkyl, branched or unbranched carbon chain containing 1 to 20 carbon atoms.

It is common practice to accelerate such reactions with a suitable catalyst or combination of catalysts. Isocyanates are very reactive and react with almost any compound having an active hydrogen atom. They will react with an alcohol to form urethanes and with amines to form substituted ureas. Isocyanates will also react with water to form carbamic acid and decompose readily to carbon dioxide and the amine. In a secondary reaction, the amine will form disubstituted urea. Furthermore, a variety of crosslinking reactions take place depending on reaction conditions and the use of different kinds of catalysts. The structure of the alcohol and the isocyanate also plays an important role in directing the reaction which includes, for example, urethane-isocyanate, urea-isocyanate, and trimerization reactions. Even polymerization is known. These phenomenons take place over time and deactivate to a certain degree the reactivity of isocyanates.

According to prior art methods of forming carbamates, where an extended period of time is expected to pass between the synthesis of isocyanate and the use of the isocyanate to form carbamate, it is necessary to carefully select appropriate catalysts and catalyst combinations to drive the reaction forming the carbamate. These catalysts are used to start the reaction, decrease reaction time, and to drive the reaction in the desired direction. They are also used to overcome deactivations and competition reactions.

During the past 30 years, this type of reaction and the efficiency of tertiary amines as catalysts for the reaction, including variations according to basicity and steric hindrance of tertiary amines, have been studied. For example, Polymer Technologies Inc., a subsidiary of the University of Detroit, has conducted such a study, as well as others.

The catalytic activity of tertiary amines generally increases as the basicity of the amine increases and the steric shielding of the nitrogen in the amine decreases. Low chain alkylamines or alkylarylamines, such as triethylamine, dimethylcyclohexylamine, or dimethylbenzylamine, are usually preferred over triethylenediamine, which has extreme shielding. For example, use of low chain ethylene-containing amines as catalysts promotes urethane and urea reactions equally. In contrast, catalysts with propylene-containing groups promote the urethane reaction over the urea reaction. Catalysts with synergistic properties are derived from the group of transition metal organic compounds as well as from tin and antimony. Examples of such catalysts are dibutyltindilaurate, stannous octoate, tetrabutyltin, dibutyltinchloride, dibutyltindioleate, and equivalent lead compounds.

Since urethanes of unknown alcohols form specific physicochemical parameters, this reaction is also used to identify alcohols, preferably using phenylisocyanate to form carbamates of specific melting points, as described in "Organikum," a basic organic chemistry course, VEB Deutscher Verlag der Wissenschaften, Berlin 1967.

Reaction of halogenated derivatives of propargyl alcohol with isocyanates is described in Japanese Patent No. 3903 to Meiji Con. Co. Ltd. and U.S. Pat. No. 3,923,870 to Singer. The specific melting points of carbamates provide a convenient method for identifying individually prepared carbamates. Examples of melting points specific for individual carbamates are listed in Table I, below

TABLE I

| CARBAMATE | MELTING POINT |
| --- | --- |
| Methylphenylurethane | 47° C. |
| Ethylphenylurethane | 52° C. |
| Isopropylphenylurethane | 88° C. |
| Propylphenylurethane | 57° C. |
| Alkylphenylurethane | 70° C. |
| n-Butylphenylurethane | 61° C. |
| n-Hexylphenylurethane | 42° C. |
| Cyclohexylphenylurethane | 82° C. |
| Propargyl-2,4-dichlorophenylurethane | 73° C. |
| Propargyl-2,5-dichlorophenylurethane | 75° C. |
| Propargyl-2-chloro-6-methylphenylurethane | 102° C. |
| Propargyl-2-chloro-4-methylphenylurethane | 60° C. |
| Propargylpentylnitrilurethane | 55° C. |

In the event that the urethane is a liquid at ambient temperature, it is more appropriate to characterize the urethane by its specific properties, such as its refractive index, as listed below in Table II.

TABLE II

| CARBAMATE | REFRACTIVE INDEX |
| --- | --- |
| Propargyl-2,2-dimethylpropylurethane | $n^{20}_D = 1.4561$ |
| Propargyl-n-butylurethane | $n^{20}_D = 1.4560$ |
| Propargyl-i-butylurethane | $n^{20}_D = 1.4576$ |
| Propargyl-1-ethylpropylurethane | $n^{20}_D = 1.4572$ |
| Propargylchlorohexylurethane | $n^{20}_D = 1.4859$ |
| Propargyltrifluoromethylcyclohexylurethane | $n^{20}_D = 1.4450$ |

Iodination of the final urethanes can be accomplished either by (1) iodinating the available commercial propargyl alcohol according to standard methods, such as those described in *Journal of the American Chemical Society*, 102:4193–4198 (1980) and U.S. Pat. No. 3,923,870 to Singer, or (2) first preparing the corresponding propargylurethanes and then iodinating according to various methods, such as those described in EP 14032, DE 3921035, EP 539092, EP 513541, and U.S. Pat. No. 4,841,088 to Kusaba et al.

The resulting iodopropargyl derivatives have specific melting points which provide a convenient method for distinguishing between the derivatives. The derivatives listed below in Table III are all solids.

TABLE III

| IODOPROPARGYLURETHANE DERIVATIVE | MELTING POINT |
| --- | --- |
| Idopropargyl-m-chlorophenylurethane | 75° C. |
| Iodopropargylphenylurethane | 145° C. |
| Iodopropargyl-3-nitrophenylurethane | 151° C. |
| Iodopropargyl-4-nitrophenylurethane | 170° C. |
| Iodopropargyl-3-methoxyphenylurethane | 108° C. |
| Iodopropargylmethylurethane | 56° C. |
| Iodopropargylbutylurethane | 67° C. |
| Iodopropargyl-t-butylurethane | 84° C. |
| Iodopropargylcyclohexylurethane | 120° C. |
| Iodopropargyldodecylurethane | 56° C. |

All iodopropargyl urethanes have fungicidal properties. However, halo-organic derivatives are subject to photo-oxidation when exposed to light. Photo-oxidation is a natural result of entropy which promotes the reassimilation of carbon back into the carbon cycle. In particular, halo-substituted organic compounds are likely to decompose when exposed to sunlight. Organic halogenic compounds, particularly chlorine, bromine, and iodine organics, form fragments of free radicals following the absorption of ultraviolet (UV) light.

Iodoorganic compounds, depending on the intensity, wavelength, and exposure time of UV light, form elemental iodine as well as other free radical fragments following UV absorption. Elemental iodine, like bromine, is yellow to brown in color. Thus, UV light exposure causes discoloration and yellowing in iodoorganic compounds as they undergo photo-oxidation and form elemental iodine and other free radical fragments. This phenomenon is exhibited by iodopropargylbutylurethane, also known as 3-iodo-2-propynylbutyl carbamate, abbreviated "IPBC" a common preservative used in paint compositions.

There are several prior art methods for preventing discoloration caused by formation of elemental iodine in response to absorption of UV light, with varying levels of success. Various research groups have discovered that the higher the iodine ratio in an iodine organic compound, the more likely the tendency to form radicals, and eventually elemental iodine, under UV light radiation. This is expected for di- and particularly tri-iodoalkyl alcohol as well as triiodoalkyl derivatives. Of all the tested materials, triiodoalkylalcohol breaks down the easiest through photoirradiation.

One known approach to avoiding discoloration and yellowing is the addition of up to 20% by weight of an organic epoxide stabilizer which apparently functions as a hydrogen iodide acceptor. These epoxy-based acid scavengers include epoxides of vegetable oils and fats, aliphatic resins, cycloaliphatic resins, and aryl resins. Also, epoxy derivatives, such as propylene oxide, styrene oxide, butylene oxide, and epichlorhydrin can be used. Various examples are described in U.S. Pat. No. 4,297,258 to Long, Jr. This method has only been mildly successful in preventing discoloration and yellowing.

A second known approach for preventing discoloration employs epoxides as color stabilizers for iodoalkynyl carbamate fungicides in paint compositions and coatings. Such coatings are prepared incorporating epoxides, such as 25% epichlorohydrin based on the amount of carbamate. As stated in U.S. Pat. No. 4,276,211 to Singer et al., this method of preventing discoloration has a color rating of 2 on a scale of 1 to 5 (1=white, 5=dark yellow), as opposed to a rate of 5 without epoxide.

A third method for preventing photochemical breakdown and resulting discoloration employs UV-stabilizers of the chemical nature of triazoles or hindered amines. Examples of both classes are benzotriazole and bis-(1,2,2,6,6-pentamethyl-4-piperdinyl)( 3,5-butylpropanedioate) (see Peter D. Gabriel and Robert M. Iannucci, "Protection of Mildewcides and Fungicides From Ultraviolet Light Induced Photo-Oxidation," *Journal of Coatings Technology*, Vol. 56, No. 712, pp. 33–38 (May 1984)). According to thin layer chromatography and bioassay analysis, photochemical breakdown is prevented by using 0.5% to 2% stabilizing agent.

The above-mentioned prior art methods require one or more catalysts to form carbamate and require additional treatment, for example use of additives, to prevent discoloration and yellowing of materials incorporating the carbamate due to photo-oxidation. It is therefore desirable to provide an economical, effective method for preparing carbamates that eliminates or reduces the need for a catalyst and prevents photochemical breakdown and resulting discoloration without requiring additional treatment.

SUMMARY OF THE INVENTION

The present invention provides a method for preparing 3-iodo- 2-propynylbutyl carbamate (IPBC) without using a trialkylamine catalyst to prevent discoloration due to photochemical breakdown. The resulting inventive IPBC can be used to prevent discoloration and yellowing of technical grade material and can be incorporated in white or light-colored paint compositions to prevent discoloration and yellowing. Under the inventive reaction conditions discussed below, periodinated by-products, which have a high tendency to breakdown when exposed to UV light, are rarely formed, thereby preventing the discoloration and yellowing that normally results from UV irradiation.

According to the present invention, freshly distilled isocyanates are used to prepare IPBC, thereby eliminating the need for a catalyst, such as a trialkylamine catalyst. Alternatively, relatively small amounts of tinorganic catalysts can be used to drive the reaction to form the desired carbamate, which then is subject to iodination to form IPBC.

DETAILED DESCRIPTION OF THE PREFERRED EMBODIMENTS

In describing preferred embodiments of the present invention, specific terminology is employed for the sake of clarity.

However, the invention is not intended to be limited to the specific terminology so selected, and it is to be understood that each specific element includes all technical equivalents which operate in a similar manner to accomplish a similar purpose.

According to the present invention, freshly distilled isocyanate is reacted with alkynol to form the urethane and subsequently to form IPBC. The freshly distilled isocyanate does not undergo substantial self-deactivation, and does not require use of any highly-activating trialkylamine catalysts to start the reaction or drive it in the desired direction. Also, use of freshly distilled isocyanate does not require use of a synergistic combination of trialkylamine and tinorganic compounds as catalysts, as required by the prior art methods discussed above.

As used herein, the term "freshly distilled isocyanate" means isocyanate prepared by distillation within preferably about 24 to 120 hours prior to reaction with alkynol to form IPBC, and most preferably within about 24 hours prior to reaction with alkynol to form IPBC.

Specific examples of the alcohol employed in this invention are derived from alkynols of the general formula:

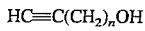

$HC\equiv C(CH_2)_n OH$ where n is a whole number of 1 to 3, for example 2-propyn-1-ol, 3-butyn-1-ol, and 4-pentyn-1-ol, or halogenated derivatives thereof. The isocyanates employed in this invention have the general formula:

$R(NCO)_m$ where R is an unsubstituted or substituted alkyl, cycloalkyl, branched or unbranched carbon chain containing 1 to 20 carbon atoms and having m=1 to 3 functional isocyanate groups. Specific examples of such isocyanates are methylisocyanate, ethylisocyanate; propylisocyanate, n-butylisocyanate, t-butylisocyanate, pentylisocyanate, hexylisocyanate, octylisocyanate, dodecylisocyanate, octadecylisocyanate, and cyclic or branched isocyanates, for example cyclohexylisocyanate.

Preferably, 3-iodo-2-propynylbutylcarbamate (IPBC) is prepared by first reacting 2-propyn-1-ol with freshly distilled butylisocyanate according to the following formula:

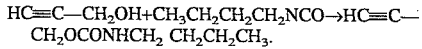

$HC\equiv C-CH_2OH+CH_3CH_2CH_2CH_2NCO \rightarrow HC\equiv C-CH_2OCONHCH_2 \ CH_2CH_2CH_3.$ Then, the resulting 2-propynylbutylcarbamate is iodinated in the presence of alkalihydroxide using a standard iodination step according to the following formula:

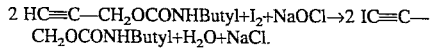

$2\ HC\equiv C-CH_2OCONHButyl+I_2+NaOCl \rightarrow 2\ IC\equiv C-CH_2OCONHButyl+H_2O+NaCl.$ Very freshly distilled isocyanate (isocyanate prepared by distillation within about 24 hours before reaction with alkynol) is preferably employed at ambient temperatures between about −5° C. and 100° C. so that the reaction will start immediately.

Alternatively, catalysts selected from the group of transition metal organic compounds, as well as catalysts selected from the group of tin, antimony, and lead organic compounds, can be used to start the reaction, for example where the isocyanate was prepared within about 72 to 120 hours prior to reaction with alkynol. If such catalysts are employed, relatively small amounts, from about 0.001% by weight to about 1% by weight and preferably from about 0.01% by weight to about 0.5% by weight, are sufficient to start the reaction. Reaction times using freshly distilled isocyanate and a tinorganic compound as a catalyst are between about a few minutes and several hours, up to about 12 hours, at ambient temperatures between about −5° C. and 100° C. If the isocyanate is old (prepared by distillation more than about 120 hours before reaction with alkynol), the reaction will not start without using a prior art trialkylamine or combination catalyst to obtain reasonable yields.

When propargyl carbamate derivatives prepared according to the present invention are subjected to standard iodination in the presence of elemental iodine, hypochlorite, and alkalihydroxide, iodinated propargylalkylcarbamates can be formed in the absence of any synergistic catalysts selected from the group of low chain trialkylamines required by prior art methods. The final technical grade iodopropargyl carbamate prepared according to the invention exhibited only moderate to no yellowing when exposed to bright sunlight for several minutes. IPBC prepared according to the inventive method can be incorporated into a material, coating, or paint composition as an anti-fungal agent that will not exhibit discoloration or yellowing when exposed to ultraviolet light or sunlight.

EXAMPLE 1—COMPARATIVE TEST METHOD

Test Material: IPBC Made with and without Trialkylamines

To perform a comparative test, a first sample of IPBC was prepared according to prior art methodology with a trialkylamine combination catalyst comprising trialkylamine and dibutyltindilaurate, and a second sample of IPBC was prepared according to the invention without a trialkylamine or combination catalyst.

About 1 g. of each sample was placed on a white piece of paper and exposed to the bright sunlight at noon time for about 5 minutes. The color change from white to yellow was recorded. After the 5 minutes expired, the prior art sample including a combination catalyst turned bright yellow.

The sample prepared according to the invention (IPBC prepared without a trialkylamine catalyst) remained white, exhibiting only a negligible color shift to a light yellow appearance.

EXAMPLE 2

Test material: IPBC Made with and without Trialkylamines

In a second experiment, 0.3% to 0.5% by weight of each of the samples prepared for Example 1 was incorporated into a standard white latex paint, and the paint was applied to test panels. The coated test panels were exposed to bright sunlight for about four hours. The inventive sample (IPBC prepared using the standard iodination method without a trialkylamine catalyst) did not exhibit any yellowing, whereas the prior art sample prepared with conventional IPBC containing a trialkylamine combination catalyst comprising trialkylamine and dibutyltindilaurate exhibited a slight discoloration to a light yellow shade. This discoloration vanished after the sample was removed from sunlight for about two days.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. An improved method for preparing 3-iodo-2-propynylbutylcarbamate of the type where 2-propyn-1-ol is reacted with butylisocyanate to form 2-propynbutylcarbamate and the 2-propynylbutylcarbamate is iodinated to form 3-iodo-2-propynylbutylcarbamate; wherein the improvement comprises preparing the butylisocyanate by distillation within about 24 hours prior to reaction with the 2-propyn-1-ol and carrying out the reaction in the absence of a trialkylamine catalyst.

2. An improved method for preparing 3-iodo-2-propynylbutylcarbamate of the type where 2-propyn-1-ol is reacted with butylisocyanate and a catalyst selected from the group consisting of organometallic compounds to form 2-propynbutylcarbamate and the 2-propynylbutylcarbamate is iodinated to form 3-iodo-2-propynylbutylcarbamate; wherein the improvement comprises preparing the butylisocyanate by distillation within about 120 hours prior to reaction with the 2-propyn-1-ol and carrying out the reaction in the absence of a trialkylamine catalyst.

3. The method of claim 2, wherein said catalyst comprises dibutyldilaurate.

* * * * *

UNITED STATES PATENT AND TRADEMARK OFFICE
CERTIFICATE OF CORRECTION

PATENT NO. : 5,554,784
DATED : September 10, 1996
INVENTOR(S) : Rainer Gruening

It is certified that error appears in the above-indentified patent and that said Letters Patent is hereby corrected as shown below:

In column 7, line 11, that portion of claim 1 reading "2-propynbutylcarbamate" should read -- 2-propynylbutylcarbamate --.

In column 8, lines 4-5, that portion of claim 2 reading "2-propynbutylcarbamate" should read -- 2-propynylbutylcarbamate --.

In column 8, line 14, that portion of claim 3 reading "dibutyldilaurate" should read -- dibutyltindilaurate --.

Signed and Sealed this

Sixth Day of May, 1997

BRUCE LEHMAN

*Attest:*

*Attesting Officer*           *Commissioner of Patents and Trademarks*